United States Patent
Charych et al.

(10) Patent No.: US 6,180,135 B1
(45) Date of Patent: *Jan. 30, 2001

(54) THREE-DIMENSIONAL COLORIMETRIC ASSAY ASSEMBLIES

(75) Inventors: Deborah Charych; Anke Reichert, both of Albany, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/944,323

(22) Filed: Oct. 6, 1997

Related U.S. Application Data

(62) Division of application No. 08/389,475, filed on Feb. 13, 1995, now abandoned, which is a division of application No. 08/944,257, filed on Oct. 6, 1997, which is a continuation of application No. 08/389,475, filed on Feb. 13, 1995, now abandoned, which is a continuation-in-part of application No. 08/289,384, filed on Aug. 11, 1994, and application No. 08/328,237, filed on Oct. 24, 1994, now abandoned.

(51) Int. Cl.[7] .......................... A61K 9/127; A61K 39/00; G01N 33/543

(52) U.S. Cl. .......................... 424/450; 424/417; 424/420; 424/812; 935/54; 436/829; 436/518; 436/528; 436/531; 436/805; 436/164; 436/171

(58) Field of Search .............................. 422/55, 57, 58, 422/82.05, 82.09; 427/2; 428/441, 462; 436/518, 528, 531, 829, 805, 164, 171; 424/417, 420, 812, 450; 935/54

(56) References Cited

U.S. PATENT DOCUMENTS

| | | |
|---|---|---|
| 4,859,538 | 8/1989 | Ribi . |
| 5,268,305 | 12/1993 | Ribi et al. . |
| 5,415,999 | 5/1995 | Saul et al. . |
| 5,427,915 | 6/1995 | Ribi et al. . |
| 5,491,097 | 2/1996 | Ribi et al. . |
| 5,521,101 | 5/1996 | Saini et al. . |
| 5,571,568 | 11/1996 | Ribi et al. . |
| 5,618,735 | 4/1997 | Saul et al. . |
| 5,622,872 | 4/1997 | Ribi . |

FOREIGN PATENT DOCUMENTS

| | | |
|---|---|---|
| WO 96/25665 | 8/1996 | (WO) . |
| WO 97/27316 | 7/1997 | (WO) . |
| WO 98/04743 | 2/1998 | (WO) . |
| WO 98/39632 | 9/1998 | (WO) . |

OTHER PUBLICATIONS

Arisawa et al., "Quantitative characterization of enzymes adsorbed on to Langmuir–Blodgett films and the application to a urea sensor," *Thin Solid Films* 210:443–445 (1992).

Bader et al., "Liposomes from Polymerizable Glycolipids," *Chem. Int. Ed. Engl.* 20:91–92 (1981).

Bamford et al., "Stuides of a novel membrane for affinity separation," *J. Chromatography* 606:19–31 (1992).

Bamford et al., "Chemical methods for improving the haemocompatibility of synthetic polymers," *Clinical Materials* 10:243–261 (1992).

Beswick et al., "Optical Detection of Toxic Gases Using Fluorescent Porphyrin Langmuir–Blodgett Films," *J. Colloid Interface Sci.* 124:146–155 (1988).

Chance et al., "Thermal effects on the optical properties of single crystals and solution–cast films of urethane substituted polydiacetylenes," *J. Chem. Phys.* 71:206–211 (1979).

Charych et al., "A 'litmus test' for molecular recognition using artificial membranes," *Chem. And Biol.* 3:113–120 (1996).

Frankel et al., "Supramolecular Assemblies of Diacetylenic Aldonamides," *J. Am. Chem. Soc.* 116: 10057–10069 (1994).

Furuki et al., "Hybrid gas detector of squarylium dye Langmuir–Blodgett film deposited on a quartz oscillator," *Thin Solid Films* 210:471 (1992).

Hupfer et al., "Liposomes from Polymerizable Phospholipids," *Chem. Phys. Lipids* 33:355–374 (1983).

Kaneko et al., "Absorption properties and structure changes caused by pre–annealing in polydiacetylene Langmuir–Blodgett films," *Thin Solid Films* 210:548–550 (1992).

Kingery–Wood et al., "The Agglutination of Erythrocytes by Influenza Virus is Strongly Inhibited by Liposomes Incorporating an Analog of Sialyl Gangliosides," *J. Am. Chem. Soc.* 114:7303–7305 (1992).

Kuo et al., "Synthesis and Properties of Diacetylenic Glutamate Lipid Monomer and Polymer: Thermochromic Polydiacetylene Free–Standing Films," *Macromolecules* 23:3225–3230 (1990).

Mino et al., "Photoreactivity of 10,12–Pentacosadiynoic Acid Monolayers and Color Transitions of the Polymerized Monolayers on an Aqueous Subphase," *Langmuir* 8:594–598 (1992).

Miyasaka et al., "Amperometric Glucose Sensor with Glucose Oxidase Imobilized on $SnO_2$ Electrode via a Monolayer on a Photoreactive Nitrophenylazide Derivative," *Chem. Lett.*, pp. 627–630 (1990).

(List continued on next page.)

Primary Examiner—Keith MacMillan
Assistant Examiner—P. Ponnaluri
(74) Attorney, Agent, or Firm—Medlen & Carroll, LLP

(57) ABSTRACT

A direct assay is described using novel three-dimensional polymeric assemblies which change from a blue to red color when exposed to an analyte, in one case a flue virus. The assemblies are typically in the form of liposomes which can be maintained in a suspension, and show great intensity in their color changes. Their method of production is also described.

25 Claims, 5 Drawing Sheets

Figure 1:
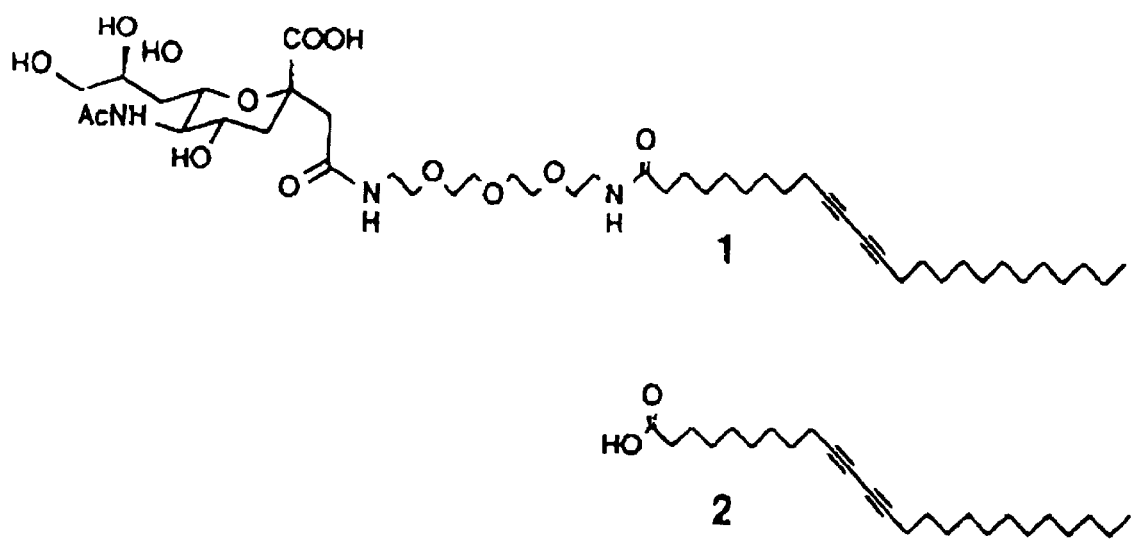
Figure 2:
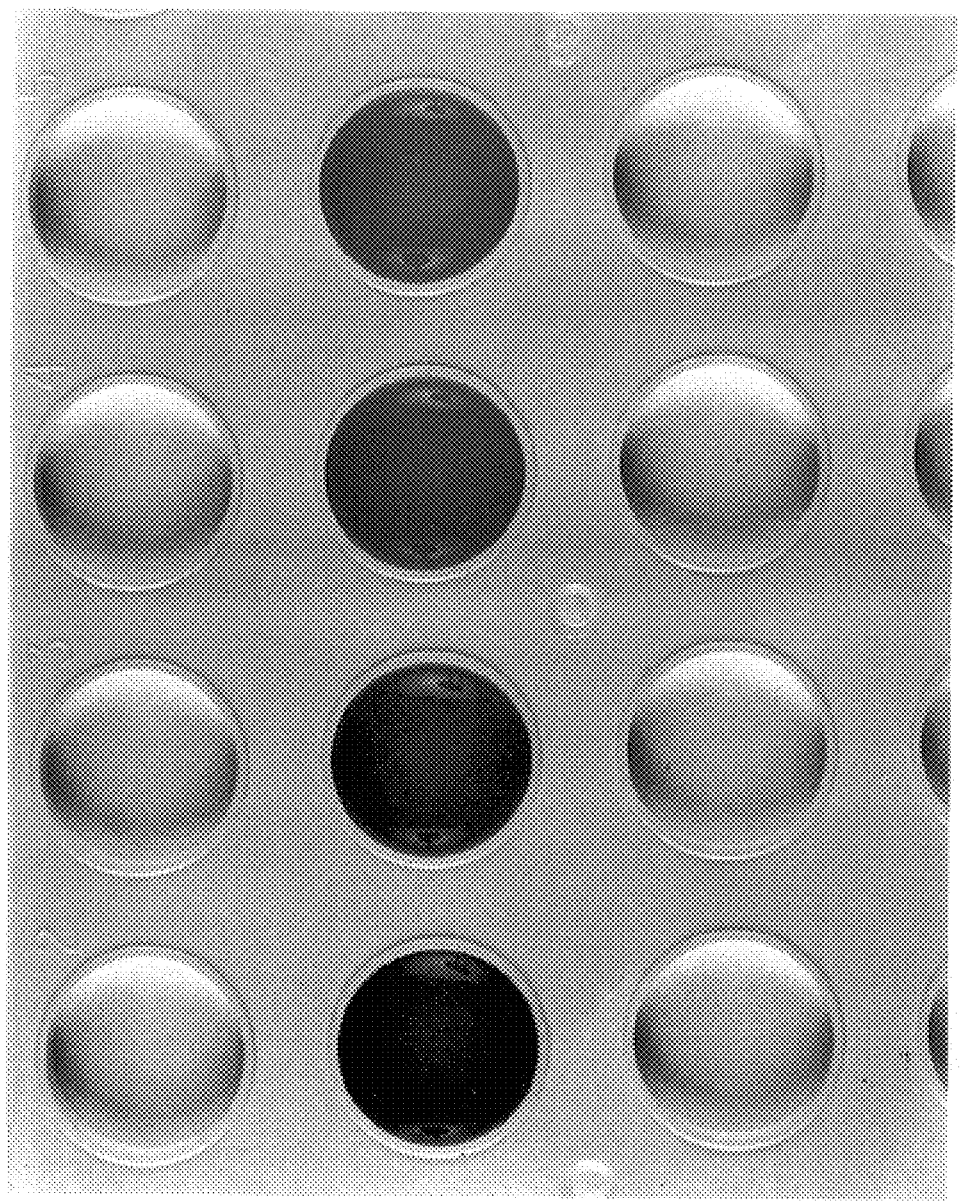

(1 of 5 Drawing Sheet(s) Filed in Color)-

OTHER PUBLICATIONS

Novotny et al., "Tribology of Langmuir–Blodgett Layers," *Langmuir* 5:485–489 (1989).

Okahata et al., "Preparations of Langmuir–Blodgett Films of Enzyme–Lipid Complexes: A Glucose Sensor Membrane," *Thin Solid Films* 180:65–72 (1989).

Ott et al., "Liposomes and influenza viruses as an in vitro model for membrane interactions II. Influence of vesicle size and preparation methods," *Eur. J. Pharm. Sci.* 6:333–341 (1994).

Reichert et al., "Polydiacetylene Liposomes Functionalized with Sialic Acid and Colorimetrically Detect Influenza Virus," *J. Am. Chem. Soc.* 117:829–830 (1995).

Rhodes et al., "Structure of Polymerizable Lipid Bilayers. 6. Bilayer Structure of Three Polymerizable Diacetylenic Glutamate Lipids," *Langmuir* 10:267–275 (1994).

Rusin et al., "Immobilization of flavoproteins on silicon: effect of cross–linker chain length on enzyme activity," *Biosensors and Bioelectronics* 7:367–373 (1992).

Shibata, "Reversible Colour Phase Transitions and Annealing Properties on Langmuir–Blodgett Polydiacetylene Films," *Thin Solid Films* 179:433–437 (1989).

Spevak et al., "Polymerized Liposomes Containing C–Glycosides of Sialic Acid: Potent Inhibitors on Influenza Virus in Vitro Infectivity," *J. Am. Chem. Soc.* 115: 1146–1147 (1993).

Swalen et al., "Molecular Monolayers and Films," *Langmuir* 3:932–950 (1987).

Whitesides et al., "Wet Chemical Approaches to the Characterization of Organic Surfaces: Self–Assembled Monolayers, Wetting, and the Physical–Organic Chemistry of the Solid–Liquid Interface," *Langmuir* 6:87–96 (1990).

Charych et al., "Specific Interaction of Influenza Virus with Organized Assemblies of Polydiacetylenes," *Mat. Res. Soc. Symp. Proc.* 282:153–161 (1993).

Charych et al., "Direct Colorimetric Detection of a Receptor–Ligand Interaction by a Polymerized Bilayer Assembly," *Science* 261:585–588 (1993).

Charych et al., "Direct Colorimetric Detection of Virus by a Polymerized Bilayer Assembly," *Mat. Res. Soc. Symp. Proc.* 330:295–308 (1994).

Pons et al., "The Optical Activity and Circular Dichroic Spectra of Diacetylenic Phospholipid Polymers," *Biochim. Biophys. Acta* 693:461–465 (1982).

New (ed.), "Preparation of liposomes," in *Liposomes A Practical Approach*, pp. 33–103, Oxford University Press (1990).

Bamford et al., "Membranes Exhibiting Molecular Recognition," *Adv. Mater.* 6: 500–502 (1994).

Downer et al., "Surface–bound biomembranes incorporating receptors: electrochemical and structural characterization," *Biosensors Bioelectronics* 7: 429–440 (1992).

Gronow, "Biosensors," *Trends Biochem. Sci.* 9: 336–340 (1984) describe types of biosensors.

Kepley et al., "Selective Surface Acoustic Wave–Based Organophosphate Chemical Sensor Employing a Self–Assembled Composite Monolayer: A New Paradigm for Sensor Design," *Anal. Chem.* 64:3191–3193 (1992).

Krämer, "Biosensors for Measuring Pesticide Residues in the Environment: Past, Present, and Future," *J. AOAC Intern.* 79:1245–1254 (1996).

Vikholm et al., "Incorporation of Lipid–Tagged Single–Chain Antibodies into Lipid Monolayers and the Interaction with Antigen," *Langmuir* 12: 3276–3281 (1996).

Tieke, "Langmuir–Blodgett Membranes for Separation and Sensing," *Adv. Mat.* 3:532–541 (1991).

Lio et al., "Atomic force microscope study of chromatic transitions in polydiacetylene thin films," *J. Vac. Sci. Technol.* 14(2):1481–1486 (1996).

Leung et al., "Imaging of polydiacetylene on graphite by scanning tunneling microscopy," *J. Appl. Phys.* 69(4):2044–2047 (1991).

Miyasaka et al., "Oriented Polypeptide Monolayers by Rapid Spontaneous Condensation of Amphiphilic Amino Acid Esters," *The Solid Films* 210/211:393–396 (1992).

Pan and Charych, "Molecular Recognition and Colorimetric Detection of Cholera Toxin by Poly(diacetylene) Liposomes Incorporating Gm1 Ganglioside," *Langmuir* 13:1365–1367 (1997).

Pan and Charych, "Molecular Recognition and Optical Detection of Biological Pathogens at Biomimetic Membrane Interfaces," *SPIE Proceedings* 40:211–217 (1997).

Charych and Nagy, "Artificial cell membranes for diagnostics and therapeutics," *Chemtech*, pp. 24–28 (1996) describe polymeric liposomes as artificial membranes that change color in response to molecular recognition at the liposome surface.

Yamanaka et al., "Solid Phase Immobilization of Optically Responsive Liposomes in Sol–gel Materials for Chemical and Biological Sensing," *Langmuir* 13:5049–5053 (1997).

Spevak, "The Presentation of Biological Ligands on the Surface of Polymerized Monolayers and Liposomes," Ph.D. Dissertation, University of California at Berkeley (1993).

THREE-DIMENSIONAL COLORIMETRIC ASSAY ASSEMBLIES

This is a divisional of application Ser. No. 08/389,475, filed on Feb. 13, 1995 now adandon.

The present application is a divisional of U.S. patent application Ser. No. 08/944,257 filed Oct. 6, 1997, which is a continuation of U.S. patent application Ser. No. 08/389,475 filed Feb. 13, 1995, now abandoned, which is a continuation in part of U.S. patent application Ser. Nos. 08/289,384 filed Aug. 11, 1994, and 08/328,237 filed Oct. 24, 1994, now abandoned.

This invention was made with Government support under Contract No DE-AC03-76SF00098 between the U.S. Department of Energy and the University of California for the operation of Lawrence Berkeley Laboratory. The Government has certain rights in this invention.

BACKGROUND OF THE INVENTION

The present invention relates to a method for direct detection of analytes using color changes in three-dimensional polymeric assemblies which occur in response to selective binding of analytes to their surface.

Analytical Chemistry

Analytical chemistry techniques have been used for many years to determine such medical parameters as hematocrit levels. While useful in their own right, analytical chemistry methods are of limited or no practical applicability to many biological parameters in which assessment would be valuable. Unless expensive and cumbersome gas chromatography methods are used, large quantities of analytes are generally required to accomplish such methods. Often, quantitative results are limited or not available. However, such techniques have been used for such basic chemical tests as creatinine assays.

Microbiological and Pathology Methods

Another approach to medical-biological systems analysis has been direct microscopic observation using various cell-staining and classic pathology techniques. Augmenting these capabilities have been well developed microbiological techniques, such as culturing, colony characterization, and observation of metabolic and nutrient limitations. Most of medical science has been developed using this basic arsenal of analytic techniques. While culturing and direct tissue observation techniques have served as the bulwark of medical detection processes for many years, they have considerable limitations.

Pathological analysis of patient tissues to determine the development of a disease state and the identification of the causative pathogen generally requires an invasive procedure. On the other hand, culturing the pathogen from various body fluid or other samples is time consuming and expensive.

Immunoassays

A breakthrough in medicine occurred with the development of immunoassay techniques. In these methods, an antibody is developed which will specifically bind to a target of interest. While costly in both their development and production, antibodies from animals allowed a very accurate analysis of a number of analytes which had previously been virtually unassessable in both research and particularly clinical situations.

An important technical advancement in immunoassay was the development of monoclonal antibodies. Instead of subjecting an animal to an analyte and harvesting its whole range of antibodies, in this techniques a single spleen cell of a sensitized animal is rendered immortal and multiplied many times. The resulting cell line is then cultured to produce a very specific and pure antibody product.

Because the antibody itself is a small molecule, it must be labeled in some way so that the binding event can be detected. This can be done with a dye, fluorescent, radioactive or other label. Conversely, if binding inhibition occurs between a known amount of introduced, labeled analyte and the material to be analyzed, the diminution of the signal will indicate the presence of test analyte. If the agglutination of the antibody particles is of sufficient volume and density, the formation of a precipitant can also serve to signal the presence of an analyte.

In recent years, the research and medical communities have come to rely heavily on immunoassay techniques to detect and quantify biological materials. While successful in many respects, the indirect nature of immunoassay methods as well as their dependence on antibody materials, results in a variety of complications, problems, and assay limitations. Briefly, the development and production of antibodies remains expensive, and these molecules are sensitive to environmental changes. Also, these systems can only detect materials against which antibodies can be produced.

Langmuir-Blodgaett Film Assays

The techniques of molecular self-assembly, such as that described by Swalen et al., (*Langmuir,* Vol. 3, page 932, 1987) as well as Langmuir-Blodgett (LB) deposition (Roberts, Ed. Langmuir-Blodgett Films, Wiley, N.Y., 1966) have been used for coating surfaces with a well-defined, quasi two-dimensional array of molecules. The initial use for this new advancement was for materials science applications such as wetting (Whitesides, et al., *Langmuir,* Vol. 6, p. 87, 1990) and friction (Novotny et al., *Langmuir* Vol. 5, p. 485, 1989).

These bilayer films are also used as immobilizing supports for analytic reactions. Bio-sensors based on LB films can detect molecules of diagnostic significance such as glucose (Okahata, et al., *Thin Solid Films,* Vol. 180, p. 65, 1989) and urea (Arisawa, et al., *Thin Solid Films,* Vol. 210, p. 443, 1992). In these cases, classic analytical chemistry systems are immobilized on the films in order to improve the readout of the test results and otherwise simplify and improve the detection capabilities of the test procedure.

The detection of receptor-ligand interaction is generally accomplished by indirect assays such as the enzyme-linked immunosorbent and radio-labeled ligand assay. Although biotechnological functionalized films have led to elegant examples of molecular recognition at an interface, the problem of transducing the molecule recognition event into a measurable signal has remained a difficulty until the advent of the subject invention.

In the case of biosensor devices, detection is generally carried out by coupling the LB films to a secondary device such as an optical fiber (Beswick, *Journal Colloid Interface Science,* Vol. 124, p. 146, 1988), quartz oscillator (Furuki et al., *Thin Solid Films,* Vol. 210, p. 471, 1992), or electrode surfaces (Miyasaka, et al., *Chemical Letters,* p.627, 1990).

Some of the analytes bound films provide for fluorescent label, where the fluorescence or its quenched state indicate the occurrence of a binding event (Beswick, *Journal Colloid Interface Science,* Vol. 124, p. 146, 1988). In some cases, these detection materials have been embedded in the surface of the supporting bi-lipid layer (Tieke, *Advanced Materials,* Vol. 3, p. 532, 1991).

Polydiacetylene films are known to change color from blue to red with an increase in temperature or changes in pH due to conformational changes in the conjugated backbone (Mino, et al., *Langmuir,* Vol. 8, p. 594, 1992; Chance, et al., *Journal of Chemistry and Physics,* Vol. 71, p. 206, 1979; Shibutag, *Thin Solid Films,* Vol. 179, p. 433, 1989; Kaneko, et al., *Thin Solid Films,* Vol. 210, p. 548, 1992).

Functionalized Liposomes

Unpolymerized liposomes expressing sialic acid residues have been extensively used as model systems to study the interaction between influenza virus and cell surfaces (Ott, et al., *European Journal of Pharmacological Science,* Vol. 6, p 333, 1994). These liposomes are typically made of such lipid materials as cholesterol and egg phosphatidylcholine (Kingery-Wood, et al, *Journal of the American Chemical Society,* Vol. 114, p 7303, 1992).

In a publication which serves the basis for a U.S. Patent Application from which the subject application depends, is described a therapeutic functionalized liposome which is produced through polymerization. The standard in the field is to progress with the polymerization procedure until the materials are fully red, indicating that the polymerization is complete. This was the procedure used in the above cited publication.

While it has been a goal of the research community to exploit this characteristic in the detection of binding events, researchers have yet to develop a method using this phenomenon in practical applications.

GENERAL DESCRIPTION OF THE INVENTION

The present invention allows direct detection of small molecules, pathogens, bacteria, membrane receptors and drugs, by the observation of color changes which occur when these analytes bind to the inventive three-dimensional polymeric assemblies. This technological advancement represents a dramatic improvement in results over the inventors 2-D prior monolayer film work, in that the color intensity is dramatically improved. Additionally, the present work enjoys the many advantages which accrue when a test system can be suspended in fluid or bound to various supports.

It is an object of the present invention to assay the presence of biomolecules by directly detecting the binding event when the analytes specifically binds to three-dimensional polymeric assemblies.

It is a further object of the present invention to provide for the direct detection of viruses, bacteria, parasites, and other pathogens, and drugs, hormones, cell wall fragments, membrane fragments, membrane receptors, enzymes, and other biologically relevant materials using the inventive assay system.

It is another object of the present invention to provide for the development and improvement of drugs by observing competitive inhibition of natural binding events between all surfaces or binding cites and their natural bioactive ligand.

It is yet another object of the invention to provide means of testing libraries of materials, as the binding can be observed and the relevant liposome with its relevant ligand segregated from the others by segregating out a particular polymeric structure.

The present inventive assay means and method provide for the direct colorimetric detection of a receptor-ligand interaction using a novel three-dimensional polymeric assemblies system. Using the inventive method of producing these original assemblies, a ligand or its derivative is rendered polymeric by polymeric linking of the ligands through a linking arm, or through direct incorporation during the polymerization process. Some of these aspects of the present invention are described in the inventor's recently published communication, incorporated by reference herein, (Reichert et al, *J. Am Chem. Soc.,* Vol. 117, p 829, 1995).

The presence of an analyte which binds to the incorporated ligands can be detected by observing changes in the spectral characteristics of the polymeric assemblies. The polymer-ligand assembly thus encompasses a molecular recognition site and a detection sites, all within a single molecular assembly.

In one embodiment of the invention, chromatic polydiacetyle liposomes are produced, and placed in a liquid. The test sample is added. The color change which occurs indicates the presence of the analyte, and the intensity of the color allows a quantification of the analyte's concentration.

In the liposome embodiment of the present invention, the inventors have prepared synthetic, polymerizable liposomes that resemble the organization and functionalization of cell membranes and have employed them as simple colorimetric sensors. The liposomes were designed to specifically bind to influenza virus particles and, in addition, report the binding event by undergoing a visible color change. In effect, these molecular assemblies mimic cell surface molecular recognition as well as signal transduction.

In order to impart both molecular recognition and detection functions to the liposomes, the inventors combined a known ligand—receptor interaction with the unique optical properties of polydiacetylenes. The conjugated backbone of alternating double and triple bonds gives rise to intense absorptions in the visible spectrum. In single crystals or Langmuir-Blodgett films, these materials are known to undergo blue to red color transitions due to a variety of environmental perturbations including heat, mechanical stress, pH, and solvent.

In one embodiment of the subject invention, the inventors have demonstrated that specific binding of influenza virus to functionalized polydiacetylene liposomes produces an analogous color transition. In earlier work, the inventors showed that similar effects can be obtained with functionalized 2-D polydiacetylene Langmuir-Blodgett films. (Charych, et al., *Science* Vol. 261, p 585, 1993).

Influenza virus particles are enveloped by a lipid bilayer to which the hemagglutinin (HA) lectin is anchored. HA binds to terminal alpha glycosides of sialic acid on cell-surface glyco-proteins and glycolipids, initiating cell infection by the virus. As described in the prior art section of the subject application, liposomes expressing sialic acid residues have been extensively used as model systems to study the interaction between influenza virus and cell surfaces. The polymerized liposomes of the subject invention, however, are composed of molecules that allow direct visualization of this specific interaction.

Advantages of the Invention

Analytical Chemistry Techniques

Analytical chemistry techniques are the only assay system prior to the advent of the subject invention that allows direct detection. Unfortunately, analytical chemistry have limited applicability to many biological system's assay needs. Unless expensive and cumbersome gas chromatography methods are used, large quantities of analyte are required. Often, quantitative results from such methods are limited or not available. However, such techniques have been used for such tests as hematocrit analysis, and creatinine assays.

Analytical chemistry methods are virtually unavailable for most biological molecules due to the destruction of the analyte's characteristics during preparation and analysis steps, and the typically small amount of the analyte present in the test sample. For these reasons, the advent of immunoassay techniques was revolutionary in the biological sciences.

Immunoassays

Many small biological molecules are notoriously difficult to assay in a direct manner due to the severe limitation of environmental ranges which they can tolerate without losing their specific characteristics. For these among other reasons, immunoassays have been heavily relied upon to assay these classes of materials. While successful in many respects, the indirect nature of immunoassay methods results in a variety of interferences, complications, problems, and assay limitations.

The requirement that an antibody be developed and produced for each possible target limits the efficacy of immunoassay methods in such applications as designer drug development and screening. Ironically, while allowing testing within a portion of biological environmental ranges, the large glycoproteinaceous antibodies are often highly sensitive to degradation outside of a small testing parameter environmental range. Thus, the susceptibilities of antibodies too rigorously limit the environmental testing range available in these assay systems.

A subtle disadvantage to immunoassay systems occurs in rapidly evolving pathogens such as the influenza virus. In such organisms, especially in the case of viruses, the external coat which is available for immune reactions constantly shifts its antibody recognition elements. Thus, despite a full blown immunity response to an influenza strain, within months an individual can again develop flu, but from a pathogen with an external coat so modified that it is immunologically unrecognizable by the victims memory cells. This is the reason individuals can develop flu year after year.

Unique Qualities of the Present Invention

The present invention enjoys the unique advantage over both immunumoassay and analytical chemistry techniques of directly detecting biological analytes. In contrast to assays requiring binding to immunoglobulins, in one embodiment of the present invention, the host attachment site on the pathogen is exploited for recognition function. This site, generally in an immunologically inaccessible valley on the pathogen surface, is highly genetically conserved over time. The minimal variability of this site is necessary for the pathogen to maintain its infectivity. As a result, a single assay system of the present invention will provide effective assays for a panoply of influenza strains, many of which may be very newly evolved.

There are many advantages to the genetically conserved host recognition site being targeted by the embodiment of the present invention. A determination of a patient's exposure to the flu will be definitive, and not limited to a particular strain. This advantage of the present invention also avoids the need for a large number of immunological tests, as the clinician can rely on a single assay. Additionally, even newly evolved, uncharacterized flu strains can be identified, further avoiding false negative tests.

An analogous limitation of immunoassays occurs in well established pathogens such as malaria parasites. In these organisms, phases of the life cycle which would allow for an immune response have over time been so limited as to avoid the immune response, or have been made to occur within host cells so as to avoid an antibody reaction.

The present invention exploits the genetically conservative host binding site to identify the pathogen. Even in comparatively large parasites, the host binding site tends to be held constant over time throughout the generations of pathogens. Additionally, parasites are usually present in the body in a large number of diverse life stages. In well established parasites, the immune accessible sites often vary considerably from stage to stage, the advantage being that the host organism is unable to mount a immunological response with sufficient rapidity to avoid the entrenchment of the parasite.

General Advantages of the Invention

The subject invention represents a dramatic advancement over both prior art direct chemical and immunoassay systems, achieving advantages which, prior to the present invention, where available exclusively in only one or the other of these analytic art methods. Much as the advent of immunoassay techniques revolutionized medical and research analytical capacities, the subject invention represents a critical advance in the analytical arts.

The present invention allows the advantages of both immunoassay and chemical analysis in a single system. The present invention enjoys the direct assay advantages of analytical chemistry methods, with many of the advantages inherent in such systems. The inventive assay technique also has a substantial environmental range of testing beyond that of immunoassays. This allows the accommodation of various analytes in their most advantageous environmental parameters. Additionally, the present invention allows rigorous, direct analysis to occur even in very narrow environmental ranges, previously unavailable with analytical chemistry techniques. The speed and simplicity of the color change indicator of the subject invention are its hallmark advantages.

Target Materials

One of the unique advantages of the subject invention is the wide range of target materials, binding events, and biochemical reactions amenable to analysis using the inventive techniques. Many of these materials previously could not be detected using a straightforward, practical assay. The present invention allows many advantages of immunoassay systems, without the complications of immunoglobulin generation or indirect analysis.

In general, the present invention requires no pre-analysis purification step. This feature of the subject invention is due to the high specificity of the ligands incorporated into the detecting polymeric assembly. Additionally, the inventive direct assay system avoids the expense, complications, and increased inaccuracies inherent in the indirect systems currently available.

Sensitive Analytes-Gentle Testing Conditions

The inventive polymeric assemblies can employ ligands and analytes which are stable or enjoy appropriate binding characteristics in a limited in vitro or environmental range of conditions. Within in vitro range conditions, the present invention is useful in that stringent limitations even within this narrow range of conditions can be met. This allows, for instance, three dimensional conformations of sensitive biochemicals and biomolecules to be maintained throughout the testing procedure.

The present invention functions well even in carefully limited conditions. Thus, conditions such as pH, saline, and temperature can be carefully controlled by feedback controls, titration and other techniques without interfering with the accuracy or sensitivity of the analysis.

Because of this wide experimental range advantage of the present invention, intact cells or sensitive subcellular inclusions can be assayed without disturbing their structural integrity. The color change when the inventive assemblies bind to a surface will pinpoint the location of an analyte, such as in a tissue sample.

Subtle cellular development stages can be monitored by the present invention, such as the various stages of malaria infection. Additionally, the association between various factors can be tested or monitored even during the interaction process using the method of the subject invention.

Weak Binding Analytes-Multivalency

The multivalent feature of the polymer-linked ligands of the subject invention provides a heightened binding capacity in the case of naturally multivalent analytes. Multivalency can also be provided for limited valency analytes prior to the test procedure to imbue them with this advantage of the subject invention. The inventive exploitation of multivalency allows a specific but weak interaction to be amplified many fold.

A structural linker of sufficient length and conformability aids in allowing binding of multiple sites on the analyte even when they are conformationally separated on a curved surface. As a result of these special features, the present invention can detect many ligands previously unsuitable for assay evaluation.

The main criteria for effective indication of the presence of analyte is that the surface of the polymeric assemblies be sufficiently perturbed to produce the requisite spectral change. Binding the analyte to an immobilizing particle will serve this purpose, as it concentrates the analyte in a small area, and further provides a three-dimensional aspect over a relatively large area to even a small analyte.

A large variety of ligands can be employed in the subject invention, allowing great flexibility in detecting a multivalent test target. Ligand selection can be based on the most advantageous binding and steric characteristics, rather than compromising these factors to accommodate the test system. Thus, the most advantageous ligand can be selected based on such factors as hydrophobicity and hydrophilicity, size, position of binding site, and conflicting affinities. Ligands which can be employed in the subject invention can include carbohydrates, peptides, nucleotides, heterocyclic compounds, and other organic molecules.

Challenging Analytes

The rigor and outstanding advantages of the inventive assay system allow the detection and quantitative evaluation of materials which have been previously unachievable because of the limitations of the prior art methods.

The inventive construct and method can assay very small biological or other molecules for which antibodies can not be developed. These target materials can include organic solvents or pollutants present at extremely low levels. There are special opportunities made available by the advances achieved by the subject inventors for drug screening in both forensic and clinical applications. Inhibition techniques applied to the subject invention can allow the testing of materials which are of a tiny size or have a small number or single valiancy.

While applicants are not bound thereby, it is hypothesized by the inventors that the unexpected spectral signal achieved by the present invention is due to a physical perturbation of the polymeric assemblies which occurs as a result of the binding event. It is the case that multivalent materials, such as viruses and cell membrane fragments, can be very easily detected using the subject inventive method. Thus, multivalent materials generally elicit a particularly strong response in the subject system. This may be the case because of conformational changes introduced into the lipid bi-layer as a result of binding causing physical reconfiguration of structure.

If applicants' theory holds true, pre-binding of smaller, single valent analyte materials to a carrier may prove advantageous to increasing the efficacy of the subject invention in those cases. For instance, the analyte could be bound to a polymer or the surface of a liposome. This would concentrate the binding event on the inventive polymeric assemblies surfaces to specific points, increasing the spectral modification at each point of contact. Additionally, the curved surface of the liposome to which the analyte is attached will likely serve to tug the peripheral bound analytes away from the bilipid surface and force analytes centrally located on the liposome into the bilipid surface. This pre-binding step then can result in increased torsion, perturbation and signal generation on the bilayer surface.

Signal Observation

Various spectral changes to the bi-layer can be used to detect the presence or absence of the target material. Means of amplifying the spectral signal well known in the art, such as scintillators, can also be employed when low levels of analyte are present. Because of the empirical nature of the signal, there are many opportunities for automating the read out of the present inventive assay system.

In one particular embodiment of the present invention, a blue pink color shift can be observed simply by visual observation by the testing technician. Because of the simplicity of the observation, this function can easily be accomplished by an untrained observer such as an at-home user. Alternatively, spectral test equipment well known in the art can be employed to determine a change in spectral qualities beyond the limits of simple visual observation, including optical density to a particular illuminating light wavelength.

The subject assemblage can also be optimized in assays by binding them to any one of a number of immobilizing materials and objects. Bonding to sephadex beads, for instance, would allow flow-through and washes to be possible during the assay procedures. The inventive assemblies could even be embedded in a gel, with the analyte difussing through it, possibly with an electrical gradient.

BRIEF DESCRIPTION OF THE DRAWINGS

The file of this patent contains at least one drawing executed in color. Copies of this patent with color drawing (s) will be provided by the Patent and Trademark Office upon request and payment of necessary fee.

FIG. 1 shows a bifunctional molecule and a pentacosadiynoic acid.

FIG. 2 is a color photograph showing a suspension of the inventive liposomes before and after introducing analyte.

FIGS. 3A and 3B show the absorption spectrums of liposomes after irradiation and exposure to influenza virus.

FIG. 4 shows a plot of colormetric response of liposomes versus successive additions of influenza virus.

DETAILED DESCRIPTION OF THE INVENTION

The inventive three-dimensional polymeric assemblage allow for the direct detection of the presence of a wide range of analytes by changes in color. The results can be read by an untrained observer, and the test can be conducted in ambient conditions. Very mild testing conditions are possible, which allow the detection of small biomolecules in a near natural state, providing information as to their interactions and avoiding the risk of modification or degradation of the analyte.

The inventive polymer assemblies are composed of a three-dimensional structure, such as a liposome or tubule whose surface contains both orienting and detecting head groups. The detecting head groups are composed of a ligand specific to the analyte in question, which is bound to one terminal end of a linear structural linker. This linker, in turn, is bound to the polymeric assemblies by its second terminal end. The polymeric assembly surface is also provided with lipid ordering head groups.

FIG. 1 provides a schematic depiction of one embodiment of the present invention. Receptor-binding ligand 1 is shown attached to one terminal end of spacer molecule 3. The second terminal end of spacer molecule 3 is then attached to one of several monomers which have been polymerized into a chromatic detection element 5. These materials are then agitated while polymerization occurs, causing the formation of the polymeric structures, such as liposomes and tubules.

Lipid Ordering Groups

The lipids appear to be important in structurally ordering the three-dimensional polymeric assemblies so that binding of the analyte produces a detectable color change. Applicants hypothesize that a structuring effect of the ordering groups serves to appropriately stabilize the physical structure of the three-dimensional polymeric assemblies to facilitate color stability and polymerization. In turn, the binding of the analyte to the molecular recognition ligand groups then causes sufficient steric perturbation or stress of the structure to result in a color change. It may be that the stability and relative rigidity engendered by the ordering lipids so unites the bilayer surface, that a steric change in one area triggers a larger effect in the surface of the assemblies as a whole.

It is not certain which of the many results of binding result in the observed spectral changes. Most likely the changes are due to stresses induced by binding which changes the effective conjugation length of the polymer backbone. The inventive three-dimensional structures are highly color sensitive to a number of environmental parameters, such as heat, and these factors may be a component of the observed phenomena as well. However, the applicants are not bound to any of the above hypothesis which are simply attempts to explain the demonstrated effective assay method of the subject invention.

Previous studies have suggested that color transitions in polydiacetylenes arise from changes in the effective conjugation length of the polydiacetylene backbone and that the electronic structure of the polymer backbone is strongly coupled to side chain conformation. The inventors can only speculate at this point that specific virus-liposome interactions may serve to alter side chain conformation, reducing the effective conjugation length of the enzyme backbone. Indeed, theoretical calculations suggest that very slight around the C—C bond of the polymer backbone decrease the π electron delocalization.

Materials for use are as head groups in the present invention include —$CH_2OH$, —$CH_2OCONHPh$, —$CH_2OCONHEt$, —$CH_2CH(Et)OCONHPh$, —$(CH_2)_9OH$, —$CH_2OCOPh$, —$CH_2OCONHMe$, —$CH_2OTS$, —CH(OH)Me, —$CH_2$ $_{OCOR2}$, wherein $R_2$ is n—$C_5H_{11}$, n—$C_7H_{15}$, n—$C_9H_{19}$, n—$C_{11}H_{23}$, n—$C_{13}H_{27}$, n—$C_{15}H_{31}$, n—$C_{17}H_{35}$, Ph, phO, or o—$(HO_2C)C_6H_4$, —$OSO_2R_2$, wherein $R_2$ is Ph, p—$MeC_6H_4$, p—$FC_6H_4$, p—$ClC_6H_4$, pBr$C_6H_4$, p—$MeOC_6H_4$, m—$CF_3C_6H_4$, 2—$C_{10}H_7$, or Me—$CO_2^-M$, wherein M is H,$K^+$, $Na^+$ or $Ba^{2+}$.

The preferred materials which can be employed as head groups in the present invention are:

—$CH_2OCONHR_2$ or —$CH_2CONHR_2$ where $R_2$ is Et, n—Bu, n—$C_6H_{13}$, n—$C_8H_{17}$, n $C_{12}H_{25}$, cyclo $C_6H_{11}$, Ph, p—$MeC_6H_4$, m—$MeC_6H_4$, o—$ClC_6H_4$, m-$ClC_6H_4$, p-$ClC_6H_4$, o-$MeOC_6H_4$, 3-Thienyl, Me, Et, Ph, 1-$C_{10}H_7$, Et, Ph, $EtOCOCH_2$, $BuOCOCH_2$, Me, Et, i—Pr, n—$C_6H_{13}$, $EtOCOCH_2$, $BuOCOCH_2$, Ph, 2,4 $(NO_2)C_6H_3OCH_2$ or $CH_2CH_2OH$.

The most preferred head groups are taken from —$CH_2COX$, where X is OH, MeO or any salt thereof.

Ligand Group

The ligand group of the present invention can be of a wide variety of materials. The main criteria is that the ligand has an affinity for the analyte of choice. The ligand may be of a broad range, such as when a class of materials is to be assayed. Appropriate ligands include peptides, carbohydrates, nucleic acids or any organic molecules which bind to receptors. For instance, all influenza strains share binding sites to a host receptor molecule. Thus, this molecule can successfully be employed to screen for all influenza strains, including those which have not yet been characterized.

Ligands can also be used in the present invention when they function as competitive binders to the analyte. For instance, a pathogen could be introduced with a test material which is to be the presence of receptor molecule. In absence of this molecule, the pathogen will bind to the three-dimensional polymeric structure and produce a color. To the degree that the pathogen surface is bound to the receptor molecule introduced in the test material, the binding will be diminished. In this way, the presence of receptor molecule can be detected and quantified.

Receptor-Binding Molecules

The use of sialic acid derivatives in one preferred embodiment described in the examples below is an example of the use of receptor-binding molecules in this capacity. Receptor-binding molecules are materials on the surface of a host cell to which a pathogen attaches itself as a prelude to the infective event. Selecting these molecules at the ligand group in the present invention has many advantages over other receptor molecules.

The recognition site for these molecules tend to be highly genetically conserved in the pathogen because of its obvious criticality to survival. Therefore, different strains of the same pathogen will generally not produce a false negative when such molecules are selected as the ligand group in the subject invention. Also, receptor molecules tend to be smaller and less complex, and often less hydrophobic, than antibodies to the same analyte.

An increasing number of receptor molecules are being recognized, identified, isolated, and synthesized for a large number of pathogens. Many have been improved for use in various analytic and treatment systems. An example of this trend in research is the sialic acid derivative used in the example below of the subject invention. Examples of the receptors for a number of pathogens are provided in the application as Table 1. All of these, as well as many more, could be exploited by the method of the subject invention.

Lipid Polymerization Groups

Many different polymerizing groups have been incorporated into lipids and are shown to be effective in monolayer polymerizations. Such moieties include: acetylenes, diacetylenes, alkenes, thiophenes, imides, acrylamides, methacrylates, vinylether, malic anhydride, urethanes, allylamines, siloxanes or vinylpyridinium etc. Lipids containing these groups can be made into homopolymers or mixed polymers. The preferred group for use in this invention is the diacetylene due to its unique optical properties in the polymerized form: polydiacetylene. However, other polymerizing groups could be used when they provide an observable change in properties upon a binding event.

Forms of the Assemblies

The three-dimensional assemblies of the subject invention can be produced in any number of forms. One of the most important forms which can be produced are liposomes. Several methods for producing the subject assemblies into that particular form are fully set forth in the Example section of this application.

The liposomes of the subject invention can be formed in a number of different sizes and types. For instance, it is possible to form the liposomes as simple bi-layer structures. Additionally, they can be multi-layered, in an onion type structure. Their size can also be varied.

Numerous other shapes can also be produced. Double chains (Kuo et al, *Macromolecule,* p 3225, Vol. 23 1990), lamellae (Rhodes, et al *Langmuir,* p 267 Vol.10, 1994), hollow tubules and braids (Frankel et al, *Journal of the American Chemistry Society,* Vol. 116, 1994), among other shapes can be formed. When these assemblies are immobilized, they can collectively form even larger constructs.

One example of a successful protocol for producing the liposome embodiment of the subject invention is as follows:

mixing of the appropriate amounts of the chloroform solutions of the lipids (1–15 mM) in a small vial evaporation of the chloroform with a stream of nitrogen addition of the appropriate amount of de-ionized water (total lipid concentration 1–2 mM)

heating of the solution above the phase transition of the lipids (about 80–90° C.)

sonication of the solution for 15 minutes (probe sonicator, Fisher sonic dismembrator model 300, 50% maximum output, microtip)

filtration of the warm opaque solution through a 0.8 μm nylon filter (Gelman) to remove small titanium particles from the solution cooling of the solution for at least one hour up to one day in the fridge (4° C.)

removal of the oxygen in the solution by bubbling nitrogen through the sample for 5–10 minutes prior to polymerization polymerization of the stirred liposome solution in a 1 cm quartz cuvette with a small 254 nm UV-lamp (pen-ray, energy: 1600 μw/cm$^2$) in a distance of 3 cm in a small chamber which is purged with nitrogen 20 minutes prior to and during the polymerization to replace all oxygen and to cool the sample; polymerization times vary between 5 and 30 minutes depending on the desired properties (color, polymerization degree) of the liposomes. Other organic solvent include benzene, alcohol, cyclohexane, hexanes, methylene chloride, acetonitrile, and carbontetrachloride. Other aqueous solutions include buffer solution, cell media, physiological saline, phosphate buffered saline, Trizma buffer, HEPES, and MOPS. Other inert gases include argon. Other polymerization means include gamma irradiation, electron beam or X-rays, or other low-energy ionizing sources. In one embodiment, the polymerization is continued until the liposomes are in the blue or purple phase. In some embodiments, the cooling step is conducted at temperatures between 4° C. and −20° C. for a period of time between 5 minutes and 5 hours. Polymerization can be accomplished by gamma radiation, electron beam, or X-rays.

EXAMPLE 1

Figure 3A:
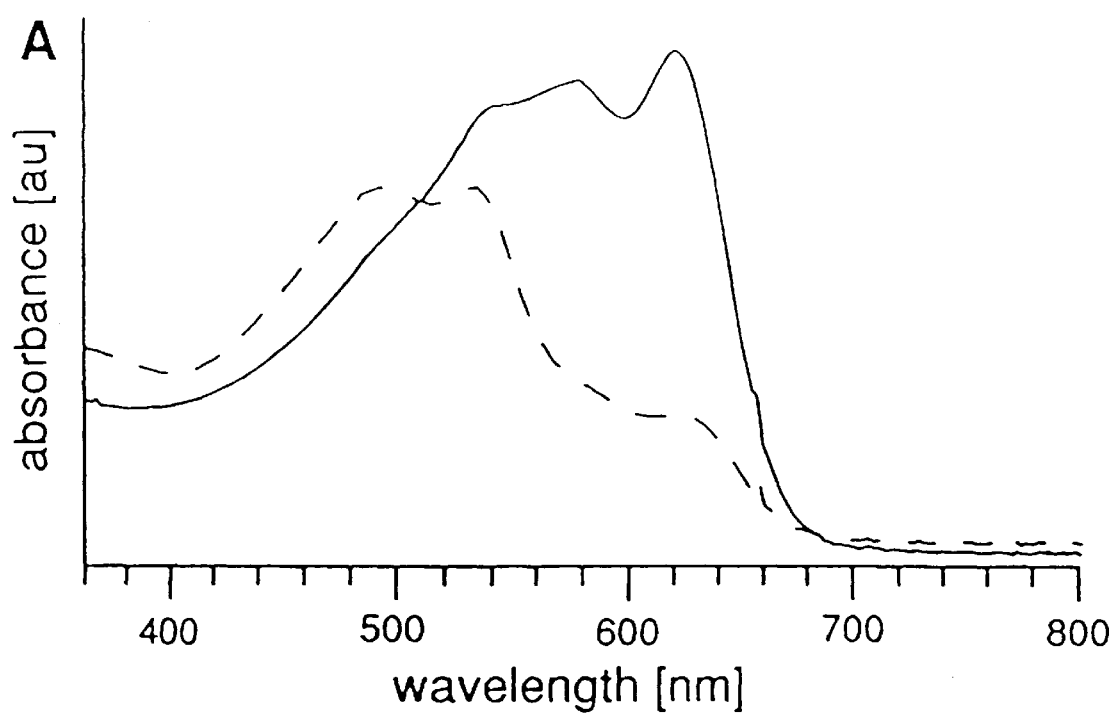
Figure 3B:
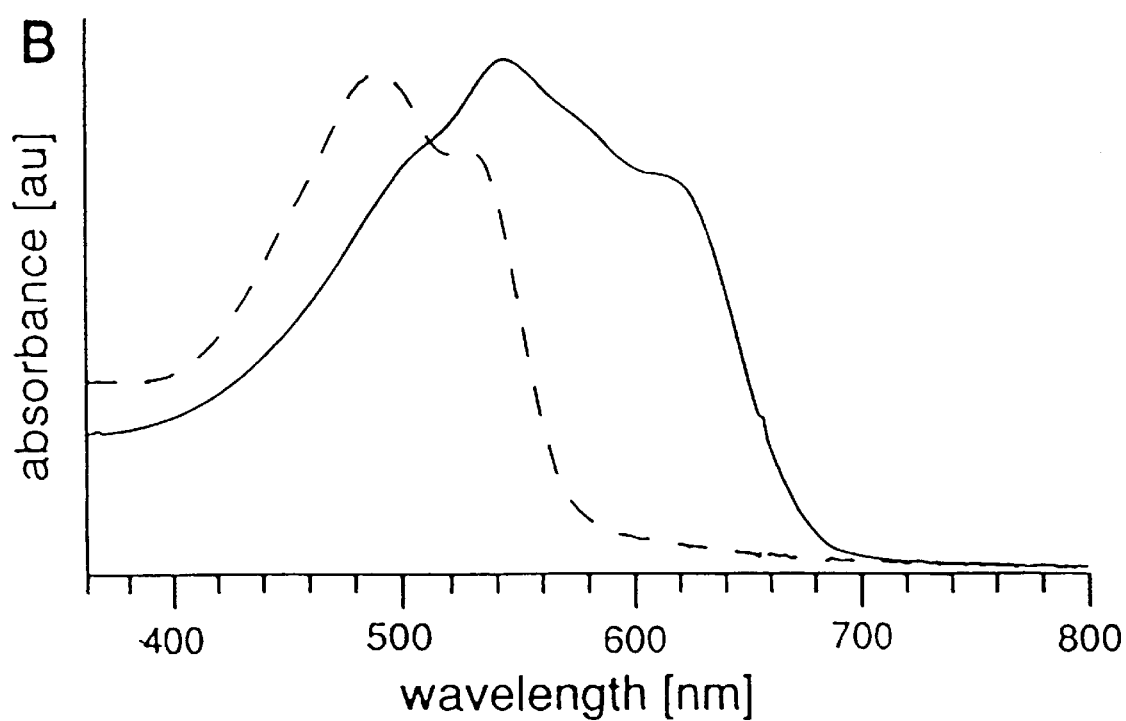

As shown in FIG. 1, the bifunctional molecule 1 use in one embodiment of the subject invention incorporates both the sialic acid ligand for viral binding and the diacetylenic functionality in the hydrocarbon chain for polymerization. The carbon-glycoside in this compound was designed to prevent hydrolysis by viral neuraminidase. This compound was mixed with 10, 12-pentasocadiynoic acid 2 and hydrated to form liposomes. Although most natural lipids that form liposomes consist of two alkyl chains, synthetic liposome-forming lipids with only one alkyl chain also exist. See, for example: Hupfer et al *Phys. Lipids,* pp 355–374 Vol. 33, and Bader, *Chem., Int. Ed. Engl.,* pp 91–92 Vol. 20, 1981. Previous studies indicated that optimum viral binding occurs for mixtures of 1–10% compound 1 in the liposome Spevak et al, *J. Am. Chem. Soc.,* 161, 115 & p. 1146, 1993. Therefore, 5% and 10% sialic acid lipid were used in this colorimetric detection study.

Liposomes were prepared using a probe sonication method, [*Liposomes: A Practical Approach;* New, Ed.; Oxford University Press; Oxford, pp 33–104, 1990,] and subsequently polymerized by irradiation at 254 nm using an ultraviolet pencil lamp. Table 1 shows colorimetric detection of influenza virus by polymerized diacetylene liposomes (5% sialic acid lipid 1), including the visible absorption spectra of (A) blue liposome solution (8 min UV) and (B) purple liposome solution (24 min UV) without virus (solid line) and after incubation with 60 HAUs of influenza virus (dashed line). The concentration of the liposome solutions in PBS buffer was 0.13 mM, and the incubation time with the virus was 1 h.

Irradiation of a liposome solution (1 mM in deionized water) for about 5–10 min results in the formation of deeply blue colored liposomes (FIG. 3A, solid line). If the polymerization time is longer (between 10 and 30 min), a purple color is observed (FIG. 3B, solid line). When influenza virus is added to the liposomes in PBS buffer, the solution immediately changes to a pink or orange color, depending on whether the initial preparation was blue or purple, respectively (FIG. 3A and FIG. 3B, dashed curves). These color changes are readily visible with the naked eye and can be quantified by visible absorption spectroscopy.

The colorimetric response (CR) is quantified by measuring the percent change in the absorption at 626 nm (which imparts the blue color to the material) relative to the total absorption maxima. In order to quantify the response of a liposome solution to a given amount of virus, the visible absorption spectrum of the liposome solution without the virus was analyzed as $$B_o=I_{626}/(I_{536}+I_{626})$$

where $B_o$ is defined as the intensity of absorption at 626 nm divided by the sum of the absorption intensities at 536 and 626 nm. The liposome solution which was exposed to influenza virus was analyzed in the same way as $$B_v=I_{626}/(I_{536}+I_{626})$$

where $B_v$ represents the new ratio of absorbance intensities after incubation with the virus. The colorimetric response (CR) of a liposome solution is defined as the percentage change in B upon exposure to virus $$CR=[(B_o-B_v)/B_o]\times 100\%$$

To be consistent with the inventors' earlier work, the absorption maxima at 626 and 536 nm was arbitrarily chosen to calculate the percentage blue absorption for the liposomes solutions. Use of the second absorption maximum at 480 nm for the calculations does not change the relative trend of the results shown.

As shown in FIG. 3, incubation of the blue liposomes (8 min UV) with 60 hemagglutinating units (HAUs) of virus leads to a CR of 47%; incubation of the purple liposomes (24 min UV) with the same amount of virus gives a CR of 87%. A hemagglutinating unit (HAU) is a measure of the highest dilution of the virus solution that still completely agglutinates a 1% solution of red blood cells. The inventors speculate that the enhanced sensitivity of the purple liposomes may be due to an increased polymer content, as suggested by their higher optical density (data not shown).

No color change could be detected if pure PBS buffer or a solution of BSA in PBS buffer (1 mg/mL) was added to the liposome solution (CR≦5% within 2 h). In order to directly address the effects of nonspecific adsorption, liposomes were prepared without sialic acid lipid (i.e., as opposed to compound 1 in FIG. 1). Similarly, these liposomes did not change color after exposure to virus.

EXAMPLE 2

The specific nature of the interaction between the influenza virus and the sialic acid liposomes was confirmed by a competitive inhibition experiment. Incubation of a liposome solution (10% sialic acid lipid 1) with 54 HAUs of influenza virus yields a CR of 31% for blue and 70% for purple liposomes. Performing the same experiment with a slight excess of α-O-methyl-neuraminic acid, a known inhibitor for influenza virus hemagglutination, results in no color change.

Figure 4:
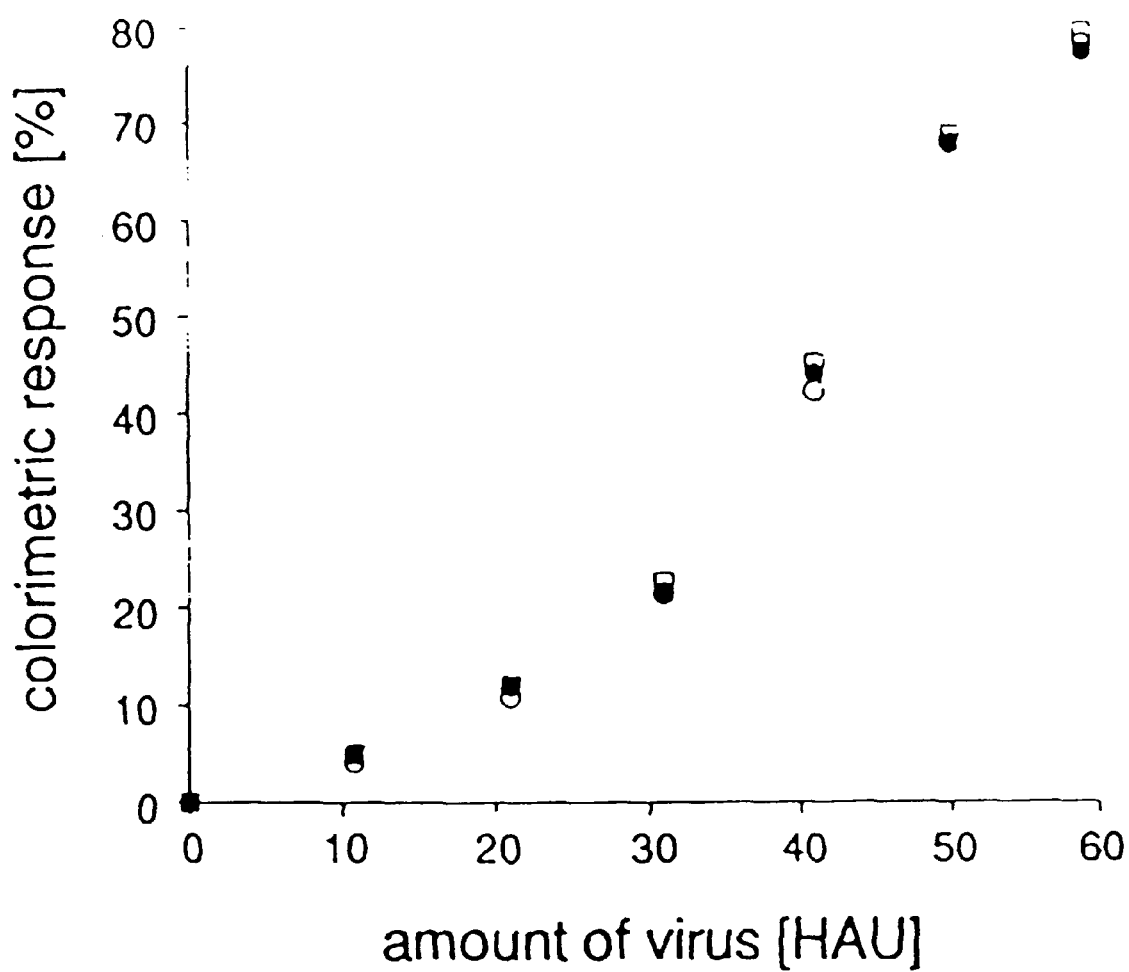

Kinetic experiments show that the color change induced by the addition of an aliquot of virus reaches a plateau after 30 min. although the change becomes apparent within 5 min. For a given polymerization time, the CR depends on the amount of added virus, as shown in FIG. 4. This figure is the plot of the colorimetric response of a purple liposome solution (5% sialic acid lipid 1, 24 min UV) versus successive additions of influenza virus. The liposomes were incubated for 30 min following each addition of virus, and the visible absorption spectrum was recorded. The CR for each virus concentration was obtained in three independent experiments.

Given that the color change of the liposomes in buffer without virus is less than 4% within 2 h, a CR of 5% or more in a few minutes is considered significant. Therefore, the amount of virus required to produce a CR just above this value defines the detection limit of the method in this particular embodiment. The titration curve in FIG. 4 shows that as little as 11 HAUs can be detected. This corresponds to approximately $11 \times 10^7$ virus particles by electron microscopy count.

The subject inventors have demonstrated that polymerized structures including liposomes are biomolecular materials that provide a molecular recognition function (sialic acid) and a detection element (polydiacetylene backbone), all within a single supramolecular assembly. The binding event is transduced to a visible color change, readily seen with the naked eye and quantified by absorption spectroscopy. Specificity of the color change was demonstrated by competitive inhibition studies. In addition, nonspecific adsorption, if it occurs, does not appear to affect the color of the liposome solutions.

EXAMPLE 3

Immobilizing Liposomes to Substrates

Attachment to membranes of poly(ether urethanes) or polyacrylonitrile. These membranes are porous, hydrophilic and can be used for affinity separations or immunodiagnosis. The liposomes can be coupled to these membranes by first attaching to the membrane an activating group such as imidizolyl-carbonyl, succinimido, FMP or isocyanate which adds rapidly to nucleophiles in the liposomes such as —NH2, —SH, —OH. Thus, any liposome preparation which contains these functionalities can be directly attached to the membrane. This procedure is analogous to the coupling of proteins to membranes the latter of which can be found in the literature. (C. H. Bamford, K. G. Al-I,amee, M. D. Purbrick, T. J. Wear, J. Chromatography, 1992, 606, 19 or C. H. Bamford, K. G. Allamee, Clinical Materials, 1992, 10, 243. In principle, any strategy previously developed to immobilize proteins can be used to immobilize liposomes.

Liposomes which have an —SH functionality can also be immobilized directly to gold surfaces, particles, or electrodes via the thiol-gold bond. In this case, a solution of the liposomes containing the —SH group are incubated with the clean gold surface in water for 12–24 hours with stirring at room temperature.

Liposomes can be immobilized to silicon chips or silica gel (silicon dioxide) using the following procedure. The gel or wafers are acid cleaned in 1:1 HCl:methanol, rinsed in water, and placed in concentrated sulfuric acid. After a thorough water rinse, the wafer chips or gel is boiled in doubly distilled deionized water, allowed to cool and dry and then silanized under inert atmosphere in a 2% solution of 3-mercaptopropyl trimethoxysilane prepared in dry toluene. Next, the chips or gels are placed in a 2 mM solution of either GMBS (N-succinimidyl 4-maleimidobutyrate) or EMCS (N-succinimidyl 6-maleimidocaproate) prepared in 0.1 M phosphate buffer (the cross linker is first dissolved in a minimal amount of dimethylformamide). After rinsing with phosphate buffer, the chips are placed in a 0.05 mg/ml solution of the liposomes prepared in pH 8.0 phosphate buffer. Finally, the chips or gels are thoroughly rinsed with, and then stored in, the buffer solution prior to their use. The liposomes should have an —NH2 functionality for the cross-linking with GMBS or EMCS to work. This procedure is a modification of a previously developed procedure which was used to immobilize enzymes to silicon chips or gels. It has been modified for the liposome immobilization. (from K. M. Rusin, T. L. Fare, I. Z. Stemple, Biosensors and Bioelectronics, 1992, 7, 367).

—NH$_2$ functionalized liposomes can also be immobilized onto surfaces by use of standard gluteraldehyde coupling reactions such as often used with the immobilization of proteins.

EXAMPLE 4

Detection and Screening

The liposomes can be used to replace standard radiolabel assays for ligand-receptor screening. For example, if the ligand is an analog of dopamine (e.g. the compound "spiperone"), the ligand can be incorporated into polymerized liposomes (polymerized assemblies). If the membrane receptor for dopamine, such as the dopamine D-2 receptor is added to the spiperone-modified liposomes, a color change from blue to pink is observed. This can be monitored spectroscopically in a manner similar to the detection of viruses and bacteria. The effect can be inhibited by the addition compounds which bind as strongly or stronger than dopamine or spiperone. By using a 96-well plate format, 96 compounds which are analogs of dopamine can be screened as potential new drugs. This high throughput screening does not require the use of expensive radiolabelled compounds and does not have the associated health and safety problems.

Procedure: Dilute 20–50 uL of liposome solution which contain from 0.5%–20% of the spiperone ligand in 100–200 uL, of an appropriately buffered medium. The solution will have a blue or purple color. The visible absorption spectrum of the sample can be recorded at this point. For detection study: add the dopamine D2 membrane receptor preparation in successive aliquots starting at 10–50 uL until 100–200 uL. The color change can be observed by eye or by recording of the visible absorption spectrum. For drug screening studies: Add the dopamine D2 membrane receptor preparation mixed with the new ligand or new drug compound. Allow for binding to occur by incubating at room temperature or at 37° C. for 5–60 minutes. Add the inhibited membrane receptor preparation to the diluted liposome solution. If the solution turns pink, the new ligand or drug was ineffective. If the solution remains blue, the new ligand or drug was an effective binder to the receptor.

EXAMPLE 5

Detection of Radioactive Metals

The monomeric diynes can be polymerized by exposure to gamma irradiation. By incorporating a ligand which is a metal chelator, the monomeric form of the liposomes are exposed to a solution of radioactive metals. Upon binding of the metal to the chelator ligand, the emitted gamma irradiation serves to polymerize the liposomes. The solution changes from a whitish opaque solution (unpolymerized liposomes) to a deep blue or deep red solution of the polymers. The liposomes serve two purposes: 1) to detect the presence of the radioactive metals, and 2) to clean the solution of the radioactive metals. Step 2 is accomplished by simply filtering or centrifuging the metal-bound liposomes. This procedure can be referred to as "seen and cleaned" since the liposomes both detect and purify the radioactive metals from the surrounding environment.

Procedure: Prepare liposomes as described up until the point of UV irradiation. The monomeric liposomes will have an opaque, whitish appearance. For detection: dilute 10–100 uL of liposomes in 50–200 uL of water or appropriate buffer. The liposomes will contain 0.5%–20% of the chelator ligand. This can be done in a 96-well plate format. Add the environmental sample to be tested, 50–100 uL. Observe the formation of a blue to red color indicating the presence of gamma irradiation, and hence the radioactive metal. For large scale cleanup purposes, the liposomes can be immobilized onto large filtration units near the efflux of wastewater treatment areas, for example, as found at Superfund clean up sites or at other United States Department of Energy facilities. The treated water passes over the filtration units. Any remaining radioactive metals in the water will be detected by a blue or red color on the filtration unit. At the same time, these metals will be cleared from the treated water such that the water can be returned to the environment or retested.

EXAMPLE 6

Glucose Sensor

The liposomes are sensitive to pH, At high pH the liposomes are in the red state and at low pH the liposomes are in the blue state. The effect can be made reversible. The liposomes can be used to detect small molecule analytes which in the presence of an appropriate enzyme or other metabolic cellular process changes the pH of its surrounding media. For example, in the detection of glucose. The liposomes are added to a media of sufficiently high pH to put them in the red state. 10–50 uL of liposomes can be diluted with 50–200 uL of the appropriate media. The test sample is added, 10–100 uL. This can be done in a 96-well plate format. To the test sample is added 10–50 uL of glucose oxidase. If glucose is present, the glucose oxidase will convert glucose to glucaraonic acid. This conversion will lower the pH of the solution, producing the blue state of the liposomes. This red to blue color change signifies the presence of glucose in the sample. The test can be done visually or quantitatively by measuring the visible absorption spectrum.

TABLE 1

| Pathogen | Receptor Molecule |
|---|---|
| HIV | D4[14]; Vasoactive Intestinal Peptide[7], Peptide T[8], Sialic Acid[12] |
| Vaccinia | Epidermal Growth Factor[1] |
| Rabies | Acetylcholine receptor[2] |
| Epstein Barr | Complement Receptor[3,4] |
| Rheo | Beta-adrenergic receptor[5] |
| Rhinovirus | ICAM-1[6,10,11]; N-CAM, myelin-associated glyeoprotein MAb[13] |
| Polio viruses | Polio viruse receptor[9] |
| Influenza | Sialic Acid[15] |
| Cytomegalovirus | Glycoprotein (not Sialic Acid)[16,17,18] |
| Coronaviruses | 9-OAC Sialic Acid & Sialic Acid |
| Encephalomyelitis | 9-OAC Sialic Acid |
| Rubella Virus | —[19] |
| Measles Virus | Glycoprotein (not Sialic Acid)[20,21,22,23] |
| Herpes | Oligosasaccharioes Glycoprotein[24,25,26] |
| Chlamydia | Sialic Acid[27,28,29,30] |
| Rhinovirus | Glycosylated Proteins[31,32] |
| Rotavirus | 9-OAC Sialic Acid |
| Polyomavirus | Sialic Acid |
| Reovirus | Sialic Acid |
| Streptococcus Suis | Sialic Acid 2 → 3 Poy-N-Acetyllactosamine |
| Salmonella Typhimurium Paramyxovirs | Sialic Acid |
| Sendl Virus | Sialic Acid |
| Mumps | Sialic Acid |
| Newcastle Disease Virus | Sialic Acid |
| Myxoviruses | Sialic Acid |
| Escherichia Coli | Oligomannose, Galactose 1 → 4 Galactose, Sialic Acid 2 → 3 Galactose |
| Encephalomyocarditis Virus | Sialic Acid |
| Choler Toxin | $G_{al}$ (A Gangliosial of Sialic Acid, Galactose, Glucose, N-Acetyl Galactos) |
| Meningitis | Sialic Acid |

[1]Nature, 381: 663 (1985)
[2]Science, 215: 182 (1982)
[3]Proc. Natl. Acad. Sci. USA, 81: 4510 (1984)
[4]J. of Biol. Chem., 265: 12293 (1990)
[5]Proc. Natl. Acad. Sci. USA, 82: 1494 (1985)
[6]Nature, 344: 70 (1990)
[7]J. of Neuroscience Research, 18: 102–107 (1987)
[8]FEBS Letters, 211: 17–22 (1987)
[9]Cell, 45: 855–865 (1989)
[10]Cell, 45: 839–842 (1989)
[11]Cell, 45: 849–853 (1989)
[12]Nature, 312: 763–770 (1985)
[13]Proc. Natl. Acad. Science, USA, 85: 7743–47 (1988)
[14]Nature, 312: 763–770 (1985)
[15]Cell, 45: 725–728 (1989)
[16]J. Virol, 63: 3991 (1989)
[17]Inas, 86: 10100 (1989)
[18]Virol, 176: 337 (1990)
[19]Med. Microbio. Imm., 179: 105 (1990)
[20]Infect. Imm., 24: 65 (1979)
[21]Proc. Soc. Exp. Bio Med, 162: 299 (1979)

TABLE 1-continued

| Pathogen | Receptor Molecule |
|---|---|
| [22]Virol, 172: 386 (1989) | |
| [23]J. Clin. Inv, 85: 2569 (1990) | |
| [24]J. Virol, 64: 2569 (1990) | |
| [25]Science, 248: 1410 (1990) | |
| [26]Febs Lett., 277: 253 (1990) | |
| [27]Infec. Imm., 57: 2378 (1989) | |
| [28]Microb. Lett., 57: 65 (1989) | |
| [29]Infect. Imm., 40: 1060 (1990) | |
| [30]Infect. Imm., 25: 940 (1983) | |
| [31]Med. Virol, 8: 213 (1989) | |
| [32]J. Virol, 64: 2582 (1990) | |

What is claimed is:

1. A method of making polymerized liposomes capable of changing color in the presence of an analyte, comprising:
   a) providing: i) a plurality of diacetylene lipid monomers; ii) one or more ligands selected from the group consisting of proteins, antibodies, peptides, carbohydrates, nucleic acids, and combinations thereof; iii) one or more organic solvents; and iv) an aqueous solution;
   b) combining said lipid monomers, said one or more ligands, and said one or more organic solvents to produce a solvent mixture;
   c) evaporating said one or more organic solvents in said solvent mixture to produce a concentrated lipid-ligand mixture;
   d) adding said aqueous solution to said concentrated lipid-ligand mixture to produce an aqueous lipid-ligand mixture;
   e) agitating said aqueous lipid-ligand mixture under conditions while maintaining a temperature above the phase transition temperature of said lipid monomers to produce an agitated lipid-ligand mixture;
   f) cooling said agitated lipid-ligand mixture to at least about 4° C. to produce liposomes; and
   g) polymerizing said liposomes to produce polymerized liposomes capable of changing color upon the binding of one or more analytes to said one or more ligands.

2. The method of claim 1, wherein said combining said lipid monomers, said one or more ligands, and said one or more organic solvents comprises covalently attaching said ligand to said lipid monomer to produce ligand-linked lipids and dissolving said ligand-linked lipids in said one or more organic solvents to produce said solvent mixture.

3. The method of claim 1, wherein said combining said lipid monomers, said one or more ligands, and said one or more organic solvents comprises dissolving said lipid monomer in a first organic solvent to produce a first mixture, dissolving said one or more ligands in a second organic solvent to produce a second mixture, and mixing said first and said second mixtures to produce said solvent mixture.

4. The method of claim 1, wherein said lipid monomers contain head groups selected from the group consisting of carboxylic acid, hydroxyl groups, amine groups, amino acid derivatives, and hydrophobic groups.

5. The method of claim 1, wherein said one or more organic solvents is selected from the group consisting of chloroform, benzene, alcohol, cyclohexane, hexanes, methylene chloride, acetonitile, carbontetrachloride, and combinations thereof.

6. The method of claim 1, wherein said aqueous solution is selected from the group consisting of deionized water, buffer solution, physiological saline, phosphate buffered saline, Trizma buffer, (N-2-hydroxyethylpiperazine-N'-2-ethanesulfonic acid), and (3-[N-morpholino]propanesulfonic acid).

7. The method of claim 1, wherein said agitated lipid-ligand mixture in step e) is filtered before cooling in step f).

8. The method of claim 1, wherein said cooling in step f) is conducted at temperatures between 4° C. and −20° C., for a period of time between 5 minutes and 5 hours.

9. The method of claim 1, wherein said cooling in step f) is conducted at temperatures between 0° C. and −15° C., for a period of time between 5 and 20 minutes.

10. The method of claim 1, wherein said cooling in step f) is conducted at temperatures between 0° C. and −5° C., for a period of time between 5 and 12 minutes.

11. The method of claim 1, wherein said polymerizing of said liposomes in step g) is conducted at temperatures between 1° C. and 22° C.

12. The method of claim 11, wherein said polymerizing of said liposomes in step g) is conducted at temperatures between 16° C. and 19° C.

13. The method of claim 1, wherein said polymerizing of said liposomes in step g) is accomplished by ultra-violet irradiation.

14. The method of claim 13, wherein said polymerizing of said liposomes in step g) is accomplished with an energy dose of 1600 $\mu$w/cm$^2$.

15. The method of claim 1, wherein said polymerizing of said liposomes in step g) is accomplished by a polymerization means selected from the group consisting of gamma radiation, electron beam, and X-rays.

16. The method of claim 1, wherein said liposomes comprise braided, lamellar, helical, and tubular shapes, and combinations thereof.

17. The method of claim 1, wherein said liposomes comprise surface functionalities selected from the group consisting of —NH$_2$, —SH, and —OH.

18. The method of claim 1, further comprising the step of providing a support, and the step of attaching said liposomes to said support.

19. The method of claim 18, wherein said support is selected from the group consisting of SEPHADEX, silica gel, SEPHAROSE, polyacrylonitriles, filters, gold, silicon chips, and silica gel.

20. The method of claim 1, wherein said agitating said aqueous lipid-ligand mixture comprises sonicating said aqueous lipid-ligand mixture.

21. A method of making polymerized liposomes capable of changing color in the presence of an analyte, comprising:
   a) providing: i) a plurality of diacetylene lipid monomers; ii) one or more diacetylene lipid monomers covalently attached to a carbohydrate; iii) one or more organic solvents; and iv) an aqueous solution;
   b) combining said lipid monomers, said one or more diacetylene lipid monomers covalently linked to a carbohydrate, and said one or more organic solvents to produce a solvent mixture;
   c) evaporating said one or more organic solvents in said solvent mixture to produce a concentrated lipid-ligand mixture;
   d) adding said aqueous solution to said concentrated lipid-ligand mixture to produce an aqueous lipid-ligand mixture;
   e) agitating said aqueous lipid-ligand mixture under conditions while maintaining a temperature above the phase transition temperature of said lipid monomers to produce an agitated lipid-ligand mixture;
   f) cooling said agitated lipid-ligand mixture to at least about 4° C. to produce liposomes; and g) polymerizing said liposomes to produce polymerized liposomes capable of changing color upon the binding of analyte to said carbohydrate.

22. A method of making polymerized liposomes capable of changing color in the presence of an analyte, comprising:
   a) providing: i) a plurality of 10,12-pentacosadiynoic acid monomers; ii) one or more 10,12-pentacosadiynoic monomers covalently linked to a sialic acid molecule; iii) one or more organic solvents; and iv) an aqueous solution;
   b) combining said lipid monomers, said one or more 10,12-pentacosadiynoic monomers covalently linked to a sialic acid molecule, and said one or more organic solvents to produce a solvent mixture;
   c) evaporating said one or more organic solvents in said solvent mixture to produce a concentrated lipid-ligand mixture;
   d) adding said aqueous solution to said concentrated lipid-ligand mixture to produce an aqueous lipid-ligand mixture;
   e) agitating said aqueous lipid-ligand mixture under conditions while maintaining a temperature above the phase transition temperature of said lipid monomers to produce an agitated lipid-ligand mixture;
   f) cooling said agitated lipid-ligand mixture to at least about 4° C. to produce liposomes; and
   g) polymerizing said liposomes to produce polymerized liposomes capable of changing color upon the binding of analyte to said sialic acid molecules.

23. A composition comprising polymerized liposomes capable of changing color in the presence of an analyte made by the method of claim 1.

24. A composition comprising polymerized liposomes capable of changing color in the presence of an analyte made by the method of claim 21.

25. A composition comprising polymerized liposomes capable of changing color in the presence of an analyte made by the method of claim 22.

* * * * *